(12) United States Patent
Dal Farra et al.

(10) Patent No.: US 8,598,124 B2
(45) Date of Patent: *Dec. 3, 2013

(54) PEPTIDES DERIVED FROM HMG-COA REDUCTASE AND COSMETIC AND/OR PHARMACEUTICAL COMPOSITION CONTAINING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/141,358

(22) PCT Filed: Dec. 23, 2009

(86) PCT No.: PCT/FR2009/001476
§ 371 (c)(1),
(2), (4) Date: Jun. 22, 2011

(87) PCT Pub. No.: WO2010/072927
PCT Pub. Date: Jul. 1, 2010

(65) Prior Publication Data
US 2011/0286991 A1     Nov. 24, 2011

(30) Foreign Application Priority Data
Dec. 23, 2008   (FR) ...................................... 08 07364

(51) Int. Cl.
| A61K 8/64 | (2006.01) |
| A61K 38/06 | (2006.01) |
| A61K 38/07 | (2006.01) |
| A61K 38/08 | (2006.01) |
| A61K 9/00 | (2006.01) |
| C07K 5/08 | (2006.01) |
| C07K 5/10 | (2006.01) |
| C07K 7/06 | (2006.01) |

(52) U.S. Cl.
USPC ....... 514/18.6; 514/18.8; 514/21.6; 514/21.7; 514/21.8; 514/21.9; 530/328; 530/329; 530/330; 530/331

(58) Field of Classification Search
None
See application file for complete search history.

(56) References Cited

U.S. PATENT DOCUMENTS

| 7,888,133 B2 * | 2/2011 | Van Venrooij et al. ....... 436/509 |
| 8,053,003 B2 | 11/2011 | Msika et al. |
| 8,147,883 B1 | 4/2012 | Msika et al. |
| 2003/0060399 A1 | 3/2003 | Brophy et al. |
| 2004/0037775 A1 * | 2/2004 | Siahaan et al. ................. 424/9.1 |
| 2008/0268077 A1 | 10/2008 | Vielhaber |

FOREIGN PATENT DOCUMENTS

| EP | 0738510 | 10/1996 |
| EP | 1272148 | 6/2006 |
| EP | 1707189 | 10/2006 |
| FR | 2789312 | 8/2000 |
| FR | 2868309 | 10/2005 |
| WO | 2004/058282 | 7/2004 |
| WO | 2005/060683 | 7/2005 |
| WO | 2007/068998 | 6/2007 |

OTHER PUBLICATIONS

Effects of Aging on the Skin from Merck Manual, p. 1. Accessed Apr. 9, 2012.*
Chronic Effects of Sunlight from Merck Manual, pp. 1-2. Accessed Aug. 23, 2012.*
Definition of "derivative" from http://cancerweb.ncl.ac.uk/omd/about.html, pp. 1-5, accessed Jul. 7, 2005.
Rudinger, J., "Characteristics of the amino acids as components of a peptide hormone sequence," Peptide Hormones, J.A. Parsons Ed., University Park Press, Jun. 1976, pp. 1-7.
"Designing Custom Peptides," from SIGMA Genosys, pp. 1-2, accessed Dec. 16, 2004.
Berendsen, H.J.C., "A Glimpse of the Holy Grail?" Science, 1998, 282: 642-643.
Voet, D. et al., Biochemistry, Second Edition, John Wiley & Sons, Inc., 1995, pp. 235-241.
Ngo, J.T. et al., "Computational Complexity, Protein Structure Prediction, and the Levinthal Paradox," The Protein Folding Problem and Tertiary Structure Prediction, K. Merc. Jr. and S. LeGrand Ed., 1994, 491-495.
Bradley, C.M. et al., "Limits of Cooperativity in a Structurally Modular Protein: Response of the Notch Ankyrin Domain to Analogous Alanine Substitutions in Each Repeat," J. Mol. Biol., 2002, 324: 373-386.
Schinzel, R. et al., "The phosphate recognition site of *Escherichia coli* maltodextrin phosphorylase," FEBS, Jul. 1991, 286(1,2): 125-128.
PCT, International Search Report, International Application No. PCT/FR2009/001476 (mailed May 7, 2010; published Jul. 1, 2010).
Gruszecka, M. et al., "Synthesis of peptides as potential antiviral agents against human rhinovirus 14," *Peptides* (1998), pp. 656-657; Proceedings of the European Peptide Symposium, 25th, Budapest, Aug. 30-Sep. 4, 1998.
PCT, International Preliminary Report on Patentability, International Application No. PCT/FR2009/001476 (Jul. 5, 2011).
Ghadially, R. et al., "The Aged Epidermal Permeability Barrier," *The Journal of Clinical Investigations, Inc.*, vol. 95, pp. 2281-2290 (May 1995).

(Continued)

Primary Examiner — Julie Ha
(74) Attorney, Agent, or Firm — Thompson Hine L.L.P.

(57) ABSTRACT

The present invention relates to peptides derived from human HMG-CoA reductase of general formula (I):

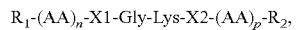

$R_1\text{-}(AA)_n\text{-}X1\text{-}Gly\text{-}Lys\text{-}X2\text{-}(AA)_p\text{-}R_2$, And of sequence SEQ ID No. 1 to SEQ ID No. 10.
The present invention also relates to a cosmetic or pharmaceutical composition comprising at least one peptide of general formula (I), in a physiologically suitable medium.
The present invention further relates to the use of this novel peptide as an active principle that activates human HMG-CoA reductase in a cosmetic composition intended to strengthen the barrier function of the skin and to stimulate epidermal differentiation. The invention further applies to a cosmetic treatment method intended to prevent and/or combat the external stresses and signs of cutaneous aging.

17 Claims, No Drawings

(56) References Cited

OTHER PUBLICATIONS

Kullmann, W., "Proteases as Catalysts for Enzymic Synthesis of Opiod Peptides," *The Journal of Biological Chemistry*, vol. 255, No. 17, pp. 8234-8238 (Sep. 1980).

Luskey, K.L. et al., "Human 3-Hydroxy-3-methylglutaryl Coenzyme A Reductase," *The Journal of Biological Chemistry*, vol. 260, No. 18, pp. 10271-01277 (Aug. 1985).

Martini, M.C., "Biochemical analysis of epidermal lipids," *Pathologie Biologie*, vol. 51, pp. 267-270 (2003).

Menon, G.K. et al., "De novo sterologenesis in the skin. II. Regulation by cutaneous barrier requirements," *Journal of Lipid Research*, vol. 26, pp. 418-427 (1985).

Norlén, L. et al., "Inter- and Intra-Individual Differences in Human Stratum Corneum Lipid Content Related to Physical Parameters of Skin Barrier Function In Vivo," *The Journal of Investigative Dermatology*, vol. 112, No. 1, pp. 72-77, (1999).

Proksch, E. et al., "Barrier function regulates epidermal lipid and DNA synthesis," *British Journal of Dermatology*, vol. 128, pp. 473-482 (1993).

\* cited by examiner

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Glu Gly Lys Gly Lys Ser Val Val Cys Glu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Glu Gly Lys Gly Lys Ser Val Val
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Asp Gly Lys Gly Lys Thr
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 4

Arg Gly Lys Ser
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 5

Arg Gly Lys Ser
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Arg Gly Lys Thr
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 7

Arg Gly Lys Thr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Lys Gly Lys Ser
1

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 9

Lys Gly Lys Ser
```

```
<210> SEQ ID NO 10
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: AMIDATION

<400> SEQUENCE: 10

Gly Lys Ser
1
```

PEPTIDES DERIVED FROM HMG-COA REDUCTASE AND COSMETIC AND/OR PHARMACEUTICAL COMPOSITION CONTAINING SAME

The present invention is situated in the cosmetic and pharmaceutical field, and more particularly in the dermatology field. The present invention relates to peptides derived from the human 3-hydroxy-3-methyl-glutaryl Co-A reductase (human HMG-CoA reductase) enzyme of general formula (I):

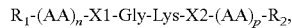

$$R_1\text{-}(AA)_n\text{-}X1\text{-}Gly\text{-}Lys\text{-}X2\text{-}(AA)_p\text{-}R_2,$$

And of sequence SEQ ID No. 1 to SEQ ID No. 10.

The present invention also relates to a cosmetic or pharmaceutical composition, comprising a peptide of general formula (I), used alone or in combination with at least one other active principle. The invention is also relative to the use of this novel peptide as an active principle that activates human HMG-CoA reductase in a cosmetic composition intended to strengthen the barrier function of the skin and to stimulate epidermal differentiation. The invention also relates to the use of this novel active principle for producing a pharmaceutical composition, in particular a dermatological composition, intended to prevent or treat pathological dysfunctions connected to an alteration in barrier function. The invention further applies to a cosmetic treatment process intended to prevent and/or combat the external stresses and cutaneous signs of aging, according to which an effective quantity of active principle, or a composition containing the active principle, is applied to the areas to be treated.

The first function of the epidermis is to constitute a barrier between the external environment and the internal environment. The outermost layer of the epidermis, the horny layer of the epidermis, ensures this function. It is composed of keratinocytes in the last stage of their differentiation, corneocytes, sealed to each other by thick intercellular cement that is both flexible and impermeable. Therefore, a cellular compartment constituted of corneocytes and an extracellular compartment mainly constituted of lipids, organized into multilamellar structures, are distinguished in the horny layer of the epidermis.

The lipid content of the human horny layer of the epidermis is estimated at 15% cholesterol ester, 16% free long-chain saturated fatty acids, 32% cholesterol and 37% ceramides, although inter-individual variations are rather significant (Norlen L. et al. J. Invest. Dermatol. 1999; 112(1) p. 72-77). These lipids are synthesized by keratinocytes from intermediate layers of the epidermis, and secreted in specialized organites called "lamellar bodies" or Odland bodies. In particular, the epidermis is a very active site for synthesizing cholesterol. The rate-limiting step of this synthesis, and the most finely regulated step, is the conversion of the 3-hydroxy-3-methylglutaryl-Coenzyme A (HMG-CoA) into mevalonate. This step is catalyzed by a membrane-bound enzyme called HMG-CoA-reductase (E.C. 1.1.1.34). Human genome sequencing data show that at least 2 isoforms for HMG-CoA reductase exist, coded by a unique gene, located on chromosome 5 (Luskey et al., J Biol. Chem., 1985 260(18), p. 10271-7).

In the skin, cholesterol plays a role in the fluidity of the membranes and, in particular, it seems to ensure the mobility of hydrocarbon chains in lipid bilayers (Martini M. C., Pathol. Biol. 2003, (51), p. 267-270). Thus, in physiological situations, cholesterol is synthesized at a level necessary for maintaining homeostasis. On the other hand, following a sudden alteration in the cutaneous barrier, a significant and rapid increase in the synthesis of cholesterol is observed, associated with an increase in the expression and activity of HMG-CoA reductase (Menon G. K. et al., J. Lipid, Res., 1985, (26), P. 418-427).

The key role of HMG-CoA reductase makes it a prime target for modulating the expression of cholesterol in the organism. Therefore, a class of pharmacological compounds intended to inhibit HMG-CoA reductase has been developed with the goal of lowering circulating cholesterol, called statins. This inhibitor effect of statins is also manifested in human skin. In fact, the experimental administration of statins by topical route disrupts the barrier function of the skin (Proksch E. et al., British J. Dermatol., 1993, (128), p. 473-482). These results confirm the importance of cholesterol in the epidermal barrier function and the central role of HMG-CoA reductase in modulating its synthesis.

When skin ages, the integrity of the skin barrier as well as its capacities for repair change. A global deficiency in lipids is observed, resulting in a reduction of lipid multilayers of the extracellular compartment of the horny layer of the epidermis. These functional changes correlate with an increased susceptibility of aged skins to external stresses (Ghadially R. et al., J Clin Invest., 1995 (95 (5), p. 2281-90).

Independently from intrinsic or photo-induced aging, alterations in the skin barrier may be produced during external stresses.

The expression "external stress" is understood to refer to stresses that the environment may produce. By way of example one may cite stresses such as pollution, UV radiation or else irritating products such as surface active agents, preservatives or fragrances, or mechanical stresses, such as abrasions, shaving or epilation. Pollution is understood to refer to both "external" pollution, due for example to diesel particles, ozone or heavy metals and to "internal" pollution, that may be particularly due to the emissions from paint, adhesive or wallpaper solvents (such as toluene, styrene, xylene or benzaldehyde), or else to cigarette smoke. Dryness of the atmosphere is also an important cause of skin stress. These external stresses result in an alteration of the barrier function that results in skin discomfort, disagreeable sensory phenomena, such as tearing pain or itching and even excessive fragility and redness.

In this context, trying to prevent the alteration or reestablish the barrier function of the epidermis is desirable. In this particular domain, the direct supply of lipid substitutes, such as ceramides (EP 1272148, US2007576937) or certain cholesterol derivatives (FR 2 789 312) has largely been described. On the other hand, the utilization of vegetable oils to activate the synthesis of cutaneous lipids has also been described. (EP 1 707 189). In the cosmetics field, the molecular targeting of HMG-CoA reductase has already been exploited in the goal of inhibiting this key enzyme, for example by utilizing statins, already known for their HMG-COA-inhibiting properties, in the goal of obtaining an anti-aging effect (EP 0738510). However, to date, no document describes or suggests that a peptide derived from human HMG-CoA reductase may have interesting properties to strengthen the barrier function of the skin and to stimulate epidermal differentiation. Activating HMG-CoA reductase in the goal of strengthening the barrier function and epidermal differentiation has now been contemplated. By this action, it is also possible to improve certain pathological dysfunctions connected to the barrier function (hypersensitive, irritated or reactive skin, atopic eczema).

The main objective of the present invention is to provide a novel active principle, capable of strengthening the barrier function of the skin, stimulating epidermal differentiation and thus preventing signs of aging of the skin or protecting the skin from external stresses. In fact, the inventors have demonstrated a cosmetic and therapeutic, and particularly a dermatological activity of peptides derived from human HMG-CoA reductase.

In particular, it has been demonstrated that these peptides, when applied to the skin, strengthen the barrier function of the epidermis and stimulate epidermal differentiation. These properties have been demonstrated by better protection of the skin tissue in relation to external stresses and by an increase in the production of lipids constituting the horny layer of the epidermis.

"Active principle that activates HMG-CoA reductase or is capable of activating human HMG-CoA" is understood to be any biologically active peptide or derivative capable of increasing HMG-CoA reductase activity, either by increasing the protein synthesis of HMG-CoA reductase (by direct or indirect modulation of the gene expression of HMG-CoA reductase), or by increasing the enzymatic activity of HMG-CoA reductase, or by other biological processes such as stabilization of the HMG-CoA reductase protein or else stabilization of messenger RNA transcripts.

Skin is understood to refer to all of the covering tissues constituting the skin and mucous membranes.

"Topical application" is understood to refer to the act of applying or spreading the active principle according to the invention, or a composition containing the principle, to or on the surface of the skin.

"Physiologically acceptable" is understood to mean that the active principle according to the invention, or a composition containing the principle, is appropriate for entering in contact with the skin without causing toxicity or intolerance reactions.

Thus, the first object of the invention is a peptide derived from human HMG-CoA reductase.

The expression "peptide derived from human HMG-CoA reductase" designates any biologically active peptide fragment in which the amino acid sequence is partially or entirely analogous or homologous to the human HMG-CoA reductase peptide sequence.

The expression "biologically active" is understood to mean "has an in vivo or in vitro activity characteristic of the activity of the active principle according to the invention."

According to a particularly advantageous embodiment of the invention, the peptide has a sequence that responds in part or in full to general formula (I)

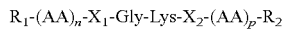

In which, $X_1$ is lysine or arginine or any amino acid, $X_2$ is serine or threonine, AA represents any amino acid, or one of its derivatives, and n and p are integers between 0 and 4, $R_1$ represents the primary amine function of the N-terminal amino acid, free or substituted by a protecting group that may be chosen from among an acetyl group, a benzoyl group, a tosyl group or a benzyloxycarbonyl group, $R_2$ represents the hydroxyl group of the carboxyl function of the C-terminal amino acid, free or substituted by a protecting group that may be chosen from among an alkyl chain from $C_1$ to $C_{20}$, or an NH2, NHY or NYY group with Y representing an alkyl chain from $C_1$ to $C_4$. The peptide is characterized in that the peptide is chosen from among the following sequences:

```
                                      (SEQ ID No. 1)
Glu-Gly-Lys-Gly-Lys-Ser-Val-Val-Cys-Glu (SEQ ID No. 2)
Glu-Gly-Lys-Gly-Lys-Ser-Val-Val (SEQ ID No. 3)
Asp-Gly-Lys-Gly-Lys-Thr (SEQ ID No. 4)
Arg-Gly-Lys-Ser (SEQ ID No. 5)
Arg-Gly-Lys-Ser-NH2

(SEQ ID No. 6)
Arg-Gly-Lys-Thr (SEQ ID No. 7)
Arg-Gly-Lys-Thr-NH2

(SEQ ID No. 8)
Lys-Gly-Lys-Ser (SEQ ID No. 9)
Lys-Gly-Lys-Ser-NH2

(SEQ ID No. 10)
Gly-Lys-Ser-NH2
```

According to a particularly interesting embodiment, the biologically active peptide corresponds to the SEQ ID No. 4 sequence.

According to another particularly interesting embodiment, the biologically active peptide corresponds to the SEQ ID No. 5 sequence.

The invention also relates to homologous forms of these sequences. The term "homologous" designates, according to the invention, any peptide sequence identical to at least 50%, or preferably at least 80%, and still more preferentially to at least 90% of said peptide sequence, chosen from among the SEQ ID No. 1 to SEQ ID No. 10 sequences. "Peptide sequence identical to at least X %" is understood to designate a percentage identity between the amino acid residues of two sequences to be compared, obtained after the optimal alignment of the two sequences. The optimal alignment is obtained by using local homology algorithms such as those used by the BLAST P or T BLAST N computer software available on the NCBI site.

The term "homologous" may also designate a peptide that differs from the sequence of a peptide of SEQ ID No. 1 to SEQ ID No. 10 sequence by the substitution of chemically equivalent amino acids, i.e., by the substitution of a residue by another having the same characteristics. Thus, conventional substitutions take place between Ala, Val, Leu and Ile; between Ser and Thr; between the acid residues Asp and Glu; between Asn and Gln; and between the basic residues Lys and Arg; Or between the aromatic residues Phe and Tyr.

In the invention, the term "amino acid" here refers to any natural or non-natural organic acid having the formula:

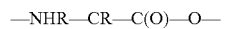

Where each —R is independently selected between a hydrogen and an alkyl group having between 1 and 12 carbon atoms. Preferentially, at least one —R group of each amino acid is a hydrogen. Here the term "alkyl" refers to a carbon chain that may be linear or branched, substituted (mono- or poly-) or non-substituted; Saturated, monosaturated (a double or triple bond in the chain) or polyunsaturated (two or more double bonds, two or more triple bonds, one or more double bonds and one or more triple bonds in the chain).

The term "peptide" designates a linkage of two or more amino acids interlinked by peptide linkages or by modified peptide linkages.

"Peptide" is also understood to refer to the natural or synthetic peptide of the invention as described above, or at least one of its fragments, whether obtained by proteolysis or synthetically, or else any natural or synthetic peptide whose sequence is partially or totally constituted by the sequence of the peptide previously described.

So as to improve resistance to degradation, it may be necessary to use a protected form of the peptide according to the invention. The form of protection must obviously be a biologically compatible form and must be compatible with a use in the field of cosmetics or pharmacy.

Many forms of biologically compatible protection may be contemplated. They are well known to the person skilled in the art as, for example, the acylation or acetylation of the amino terminal end, or the amidation or esterification of the carboxy terminal end. Thus, the invention relates to a composition such as previously defined, characterized by the fact that the peptide of SEQ ID No. 1 to SEQ ID No. 10 is in protected or unprotected form. Protection based on a substitution on the amino terminal end by an acetyl group, a benzoyl group, a tosyl group or a benzyloxycarbonyl group may be utilized. Preferably, protection based on the amidation of the hydroxyl function of the carboxy terminal end by an NYY group with Y representing an alkyl chain from $C_1$ to $C_4$, or the esterification by an alkyl group is utilized. It is also possible to protect the two ends of the peptide.

The peptide derivatives also relate to amino acids and peptides interconnected by a pseudo-peptidic linkage. "Pseudo-peptidic linkage" is understood to refer to all types of linkages capable of replacing "conventional" peptidic linkages.

In the domain of amino acids, the molecules have a geometry such that they may theoretically be present in the form of different optical isomers. Thus, there exists a molecular conformation of the amino acid (AA) that rotates the plane of polarized light to the right (dextrorotatory conformation or D-aa), and a molecular conformation of amino acid (aa) that rotates the plane of polarized light to the left (levorotatory conformation or L-aa). Natural amino acids are always of levorotatory conformation; consequently, a peptide of natural origin will only be constituted of L-aa type amino acids. However, chemical synthesis in laboratory enables amino acids with the two possible conformations to be prepared. From this base material, it is possible to incorporate, during peptide synthesis, amino acids in both dextrorotatory and levorotatory optical isomer forms. Thus, amino acids constituting the peptide according to the invention may be in L- and D- configurations; preferentially, the amino acids are in L form. The peptide according to the invention may thus be in L-, D- or DL-form.

The peptide of general formula (I) according to the invention may be obtained either by conventional chemical synthesis (in solid phase or in homogeneous liquid phase), or by enzymatic synthesis (Kullman et al., J. Biol. Chem. 1980, 225, 8234), from constituent amino acids or their derivatives.

The peptide according to the invention may be of natural or synthetic origin. Preferentially according to the invention, the peptide is obtained by chemical synthesis.

According to the invention, the active principle may be a single peptide, a mixture of peptides or peptide derivatives and/or constituted of amino acid derivatives.

According to the invention, said peptide or mixture of peptides may be utilized as a medication.

According to an advantageous embodiment of the invention, the active principle according to the invention is previously solubilized in one or more physiologically acceptable solvents, conventionally used by the person skilled in the art, such as water, glycerol, ethanol, propylene glycol, butylene glycol, dipropylene glycol, ethoxylated diethylene glycol or propoxylated diethylene glycol, cyclic polyols, white petroleum jelly, vegetable oil or any mixture of these solvents.

According to another advantageous embodiment of the invention, the active principle according to the invention is previously solubilized in a cosmetic or pharmaceutical carrier such as liposomes, or adsorbed on powdery organic polymers, mineral supports such as talcs and bentonites, and more generally solubilized in, or fixed on, any physiologically acceptable carrier.

The second object of the invention is a cosmetic, pharmaceutical, and particularly dermatological composition, comprising a peptide of general formula (I), as an active principle, used alone or in combination with at least one other active principle, in a physiologically suitable medium.

Of course, it is obvious that the invention is aimed at mammals in general, and more particularly at human beings.

According to an advantageous embodiment of the invention, the active principle according to the invention is present in the compositions of the invention at a concentration of between approximately 0.0005 and 500 ppm (parts per million), and preferentially at a concentration of between approximately 0.01 and 5 ppm with relation to the total weight of the final composition.

The usable composition according to the invention may in particular consist of a composition for hair care, and notably a shampoo, a conditioner, a treatment lotion, a styling cream or gel, a hair restructuring lotion, a mask, etc. The cosmetic composition according to the invention may be notably used in treatments implementing an application that is followed or not followed by rinsing or else in shampoo form. Thus, the active principle according to the invention may advantageously be utilized in antidandruff care of the scalp.

The active principle may also be present in the form of hair dye or mascara to be applied by brush or comb, in particular on the eyelashes, eyebrows or hair.

It is understood that the active principle according to the invention may be utilized alone or rather in combination with at least one other active principle, in a cosmetic composition or for the preparation of a pharmaceutical and/or dermatological composition. Advantageously, the usable compositions according to the invention also contain various protective or anti-aging active principles intended, in particular, for the prevention and/or treatment of disorders linked to aging.

The compositions according to the invention will be applied by any appropriate route, notably oral, parenteral or external topical, and their formulations will be adapted by the person skilled in the art, in particular for cosmetic or dermatological compositions. Advantageously, the compositions according to the invention are intended for topical administration on the skin. These compositions therefore must contain a physiologically acceptable medium, i.e., a medium compatible with the skin and epithelial appendages, and must cover all cosmetic or dermatological forms. These compositions will notably be in the form of creams, oil in water emulsions, or water in oil emulsions or multiple emulsions, solutions, suspensions, gels, milks, lotions, sticks or else powders, and suitable for an application on the skin, lips and/or epithelial appendages. These compositions comprise the excipients necessary for their formulation, such as solvents, thickeners, diluents, surface active agents, antioxidants, colorants, preservatives and fragrances.

According to another embodiment of the invention, the compositions will be appropriate for oral administration for pharmaceutical use. Thus, the compositions may in particular be present in the form of tablets, capsules, gel capsules, chewable pastes, powders to consume as is or to be mixed immediately before use with a liquid, syrups, gels or any other form known to the person skilled in the art. They will contain suitable formulation excipients, such as colorants, sweeteners, flavorings, bulking agents, binders and preservatives.

These compositions may particularly be present in the form of an aqueous solution, hydroalcoholic or oily solution; an oil in water emulsion, water in oil emulsion or multiple emulsions; They may also be present in the form of creams, suspensions or else powders, suitable for application on the skin, mucous membranes, lips and/or epithelial appendages. These compositions may be more or less fluid and have the appearance of a cream, lotion, milk, serum, pomade, gel, paste or foam. They may also be present in solid form, such as a stick, or may be applied on the skin in aerosol form. They may be utilized as a care product and/or as a skin makeup product.

These compositions also comprise any additive commonly utilized in the contemplated field of application as well as the adjuvants necessary for their formulation, such as solvents, thickeners, diluents, antioxidants, colorants, sunscreens, self-tanning agents, pigments, fillers, preservatives, fragrances, odor absorbers, cosmetic or pharmaceutical active ingredients, essential oils, vitamins, essential fatty acids, surface active agents, film-forming polymers, etc.

In all cases, the person skilled in the art will make sure that these adjuvants as well as their proportions are chosen so as to not harm the desired advantageous properties of the composition according to the invention. These adjuvants may, for example, correspond to 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

The third object of the invention is the utilization, in a cosmetic composition, of an effective quantity of peptide of general formula (I), as an active principle that activates human HMG-CoA reductase.

The effective quantity of active principle corresponds to the quantity necessary for obtaining the desired result, that is, to activate the HMG-CoA reductase, in the goal of improving the barrier function of the epidermis and stimulating epidermal differentiation.

"Strengthen the barrier function of the skin and stimulate epidermal differentiation" is understood to refer to the improvement in the protection capacity of the horny layer of the epidermis and the increase in the expression of biological differentiation markers, such as keratins.

Thus, thanks to the special properties of said active principle, it can be used in a cosmetic composition intended to strengthen the barrier function of the skin and to stimulate epidermal differentiation.

On the other hand, the peptide of general formula (I) can be used advantageously as an active principle in a cosmetic composition intended to preventively and/or curatively combat the signs of cutaneous aging, and more particularly photo-induced aging (photo aging). Cutaneous signs of aging is understood to refer to any modifications in the external appearance of the skin and epithelial appendages due to aging such as, for example, superficial roughness of the horny layer of the epidermis, wrinkles and fine lines, but also any internal modification of the skin that is not systematically manifested in a modified external appearance such as, for example, thinning of the dermis or any other internal degradation of the skin following exposure to ultraviolet (UV) radiation.

According to another aspect of the invention, the peptide of general formula (I) can be used advantageously as an active principle in a cosmetic composition intended to protect the skin against all types of external stresses.

In particular, the object of the invention is the utilization of a cosmetic composition comprising an effective quantity of peptide according to the invention to prevent or treat damage caused to the skin by mechanical treatments such as shaving or epilation.

In particular, the object of the invention is the utilization of a cosmetic composition comprising an effective quantity of peptide according to the invention to prevent or treat damage caused to the skin by extreme climactic conditions or sudden variations in temperatures and hygrometry.

The invention further consists of the utilization of the peptide according to the invention for preparing a pharmaceutical composition intended to prevent or treat pathologies characterized by an alteration in the barrier function, such as hypersensitive, irritated or reactive skin and atopic eczema.

The invention further consists of a cosmetic treatment method intended to prevent and/or combat external stresses according to which a composition comprising an effective quantity of peptide according to the invention is applied onto the areas to be treated.

The invention further consists of a cosmetic treatment method intended to prevent and/or combat cutaneous signs of aging and/or photo-aging, according to which a composition comprising an effective quantity of peptide according to the invention is applied onto the areas to be treated.

Particular embodiments of this cosmetic treatment method also result from the previous description. Other advantages and characteristics of the invention will more clearly appear upon reading the examples given for illustrative and non-limiting purposes.

EXAMPLE 1

Ultrastructural Study of Lamellar Bodies in Human Keratinocytes Treated by Peptide SEQ ID No. 5

The goal of this study is to study in an ultrastructural manner, in transmission electron microscopy, keratinocytes treated by peptide SEQ ID No. 5 at 0.5 ppm.

Protocol:

Normal human keratinocytes in culture are treated with a 1% stock solution at 50 ppm of peptide SEQ ID No. 5 for 48 hours (the medium in the presence of the active ingredient is changed every 24 hours). The cells are washed in PBS, and then are fixed by Karnosky hypertonic fixation (4% paraformaldehyde, 5% glutaraldehyde in a 0.08M phosphate buffer) 1 hour at ambient temperature and then 24 hours at 4° C. The cells are detached from the support by scraping and centrifuged 5 minutes at 1000 rpm. The supernatant is eliminated and a 1M sodium cacodylate buffer is deposited on the residue. The cells are mixed with 2% agar and then postfixed by osmium tetraoxide for 1 hour. The specimens are then dehydrated by successive passages in a series of alcohol (from 50 to 100%). The cells are then coated in a resin. The polymerization is carried out for approximately 12 hours at 60° C. Semi-thin sections of 0.5 μm are made with an ultramicrotome. The sections are deposited on a heat bonded slide and then colored with toluidine blue. The slides are then dehydrated again and mounted in a suitable medium. After having chosen the optimal study zone, the block is recut to the desired size and ultrathin sections are then made, only sections with a silver-grey color and a suitable size are mounted on the electron microscopy grid labeled with both uranyl acetate and lead citrate, and are examined by transmission electron microscope at 60 or 80 KV.

Results: The ultrastructural study shows that the Golgi complex is substantially more developed than in the control cells. This increase is connected to an excess production of lamellar bodies (or Odland bodies) that is the sign of an increase in lipid synthesis.

Conclusions: Peptide SEQ ID No. 5 at 0.5 ppm is capable of inducing an increase in lipid synthesis in normal human keratinocytes.

EXAMPLE 2

Ultrastructural Study of Caveolae in Human Fibroblasts Treated by Peptide SEQ ID No. 4

The goal of this study is to study at the ultrastructural level the caveolae in human dermal fibroblasts.

Protocol: Normal human dermal fibroblasts in culture are treated with a 1% stock solution at 50 ppm of peptide SEQ ID No. 4 for 48 hours (the medium in the presence of the active ingredient is changed every 24 hours).

Results: The ultrastructural study shows a significant increase in caveolae in cells treated by peptide SEQ ID No. 4, in comparison with untreated control cells. These results are the sign of a positive effect of the active principle, since the caveolae are invaginations of the plasma membrane that enable the externalization of molecules such as cholesterol.

Conclusions: Peptide SEQ ID No. 4 at 0.5 ppm causes the increase in membrane structures with externalization of cholesterol.

EXAMPLE 3

Differentiation Study of Human Keratinocytes Treated by Peptide SEQ ID No. 5

The goal of this study is to determine the influence of peptide SEQ ID No. 5 on epidermal differentiation.

Protocol: Normal human keratinocytes in culture are treated with a 1% stock solution at 50 ppm of peptide SEQ ID No. 4 for 48 hours (the medium in the presence of the active ingredient is changed every 24 hours). The cells are then washed and fixed with cold methanol for 4 minutes at 4° C. The cells are incubated in the presence of a monoclonal anti-cytopankeratin antibody at 1:200 for 1 hour at ambient temperature and are then revealed by a second antibody at 1:50 for 1 hour at ambient temperature, coupled with a fluorescent dye, "alexa 488." After mounting in a particular medium, the slides are observed by epifluorescence microscope.

Results: The active ingredient increases the expression of pankeratins in the treated cells.

Conclusions: Peptide SEQ ID No. 5, at 0.5 ppm, increases the expression of pankeratins in normal human keratinocytes. In the presence of peptide SEQ ID No. 5, the cells are stimulated in pathway differentiation.

EXAMPLE 4

Study of the Protective Effect of Peptide SEQ ID No. 5 on Skin Cells Subjected to Ultraviolet Radiation (UVB)

The goal of this study is to determine the protective effect of peptide SEQ ID No. 5 with relation to normal human keratinocytes subjected to stress by UVB radiation. To do this, cellular viability tests were conducted by the MTT technique.

Protocol: The normal human keratinocytes are treated with a 1% solution, a solution at 50 ppm of peptide SEQ ID No. 5, for 24 hours, irradiated by UVB (50 mJ/cm$^2$) and then cultivated again 24 hours in the presence of the same concentration of peptide SEQ ID No. 5. Untreated and irradiated controls are carried out under the same conditions. At the end of the experiment, the cells are incubated in a solution containing 0.1 mg/ml of MTT (3-[4,5-dimethylthiazol-2-yl]-2,5-diphenyltetrazolium bromide). This compound is absorbed by the living cells and then metabolized by mitochondrial enzymes into a blue violet compound, formazan, that will be assayed by spectrophotometry at 540 nm. The optical density (O.D.) Is then directly proportional to the mitochondrial enzymatic activity as well as to the number of living cells.

Results: Evaluation of cellular viability by the MTT technique shows that peptide SEQ ID No. 5 increases cellular viability after UVB irradiation by 16%.

Conclusions: Peptide SEQ ID No. 5, at the 0.5 ppm concentration, increases cellular viability and effectively protects the skin cells from the cytotoxic effects of UVB radiation.

EXAMPLE 5

Study of the Expression of HMG-CoA Reductase in Skin Biopsies in the Presence of Peptide SEQ ID No. 5

The goal of this study is to determine the influence of peptide SEQ ID No. 5 on the expression of HMG-CoA reductase.

Protocol: Samples of human skin are placed in culture at the air/liquid interface. A 1% stock solution at 50 ppm of peptide SEQ ID No. 5 is applied topically and then the samples are incubated for 24 hours or 48 hours.

These skin samples are then fixed with formaldehyde and then enclosed in paraffin. Sections of 2 to 3 μm are then made. Immunolabelling is carried out after unmasking the specific sites by microwave treatment and then incubation in trypsin. Immunolabelling is carried out by using a polyclonal rabbit antibody specific for HMG-CoA reductase (Millipore, Upstate), and then a secondary antibody, coupled with a fluorescent dye. The skin sections are then examined by epifluorescence microscope (Nikon Eclipse E600 microscope).

Results: Microscopic observations show stronger fluorescence in skin treated by peptide SEQ ID No. 5, in the upper layers of the epidermis, with relation to the untreated control.

Conclusions: Peptide SEQ ID No. 5, at the 0.5 ppm concentration, stimulates the expression of HMG-CoA reductase, in the upper layers of the epidermis.

EXAMPLE 6

Study of the Expression of HMG-CoA Reductase in Normal Human Keratinocytes in the Presence of Peptide SEQ ID No. 4

The goal of this study is to determine the influence of peptide SEQ ID No. 4 on the expression of HMG-CoA reductase in normal human keratinocytes.

Protocol: Normal human dermal keratinocytes in culture are treated with a 1% stock solution at 50 ppm of peptide SEQ ID No. 4 for 48 hours (the medium in the presence of the active ingredient is changed every 24 hours). The cells are then washed and fixed in cold methanol for 4 minutes at 4° C. The cells are incubated in the presence of a polyclonal rabbit antibody specific for HMG-CoA reductase (Millipore, Upstate), and then a secondary antibody coupled with a fluorescent dye. The cells are then examined by epifluorescence microscope (Nikon Eclipse E600 microscope).

Results: Microscopic observations show more intense cytoplasmic fluorescence in cells treated by peptide SEQ ID No. 4.

Conclusions: Peptide SEQ ID No. 4, at the 0.5 ppm concentration, stimulates the expression of HMG-CoA reductase in normal human keratinocytes.

EXAMPLE 7

Preparation of Compositions

1-Sun Protection Cream:

| Trade names | INCI names | Weight percent |
|---|---|---|
| PHASE A | | |
| Demineralized water | Aqua (Water) | qsp |
| Pemulen TR1 | Acrylates/C10-30 Alkyl Acrylate Crosspolymer | 0.40 |
| Glycerine | Glycerin | 3.00 |
| Nipastat Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoyl-methane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Peptide SEQ ID No. 4 | | 3 ppm |
| Fragrance | Fragrance | qsp |
| Colorant | | qsp |

The constituents of phase A and phase B are heated separately between 70° C. and 75° C. Phase B is emulsified in phase A under stirring. Phase C is added at 45° C., by increasing the stirring. Phase D is then added when the temperature is below 40° C. The cooling is continued until 25° C. under intensive stirring.

2-Anti-Age Cream:

| Trade names | INCI names | Weight percent |
|---|---|---|
| Phase A | | |
| Montanov 68 | Cetearyl Alcohol (and) Cetearyl Glucoside | 6.00 |
| Squalane | Squalane | 3.00 |
| Cetiol SB 45 | *Butyrospermum Parkii* (Shea Butter) | 2.00 |
| Waglinol 250 | Cetearyl Ethylhexanoate | 3.00 |
| Amerchol L- 101 | Mineral Oil (and) Lanolin Alcohol | 2.00 |
| Abil 350 | Dimethicone | 1.50 |
| BHT | BHT | 0.01 |
| Coenzyme Q10 | Ubiquinone | 0.10 |
| Phase B | | |
| Avocado oil | *Persea Gratissima* (Avocado) Oil | 1.25 |
| Phenonip | Phenoxyethanol (and) Methylparaben (and) Ethylparaben (and) Butylparaben (and) Propylparaben (and) Isobutylparaben | 0.75 |
| Phase C | | |
| Demineralized water | Aqua (Water) | qsp |
| Butylene Glycol | Butylene Glycol | 2.00 |
| Glucam E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| Peptide SEQ ID No. 4 | | 0.5 ppm |
| GP4G | Water (and) *Artemia* Extract | 1.50 |
| Collaxyl | Water (and) Butylene Glycol (and) Hexapeptide-9 | 3.00 |
| Phase F | | |
| Fragrance | Fragrance | qsp |
| Colorant | | qsp |

Prepare and melt phase A at 65-70° C. Heat phase C to 65-70° C. Phase B is added to phase A just before emulsifying A into B. At approximately 45° C., the carbomer is neutralized by adding phase D. Phase E is then added under mild stirring and cooling is continued until 25° C. Phase F is then added if desired.

3-Protective Day Cream:

| Trade names | INCI names | Weight percent |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100 cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben | 0.70 |

| Trade names | INCI names | Weight percent |
|---|---|---|
| | (and) Propylparaben (and) Isobutylparaben | |
| | Phase B | |
| Demineralized water | Aqua | qsp 100 |
| Glycerine | Glycerin | 2.00 |
| Carbopol ETD 2020 | Acrylates/C10-30Alkyl Acrylate Crosspolymer | 0.15 |
| Keltrol BT | Xanthan Gum | 0.30 |
| | Phase C | |
| Sodium Hydroxide (sol. 10%) | Sodium Hydroxide | 0.30 |
| | Phase D | |
| Demineralized water | Aqua | 5.00 |
| Stay-C 50 | Sodium Ascorbyl Phosphate | 0.50 |
| | Phase E | |
| Butylene Glycol | Butylene Glycol | 2.00 |
| Dekaben CP | Chlorphenesin | 0.20 |

| Trade names | INCI names | Weight percent |
|---|---|---|
| | Phase F | |
| GP4G | Water (and) *Artemia* Extract | 1.00 |
| Peptide SEQ ID No. 5 | | 5 ppm |

Prepare phase A and heat to 75° C. under stirring. Prepare phase B by dispersing the carbopol and then the xanthan gum under stirring. Let rest. Heat to 75° C.

At temperature, emulsify A into B under rotor stator stirring. Neutralize with phase C under rapid stirring. After cooling to 40° C., add phase D, and then phase E. Cooling is continued under mild stirring and phase F is added.

Applicants incorporate by reference the material contained in the accompanying computer readable Sequence Listing entitled "US08_111_Sequence_Listing.txt", which was created on Aug. 5, 2011, and is 2,110 bytes in size, and hereby confirm that the information recorded in the computer readable form is identical to the written sequence listing.

The invention claimed is:

1. A peptide derived from human HMG-CoA reductase, wherein the peptide is one of the following sequences:

Glu-Gly-Lys-Gly-Lys-Ser-Val-Val-Cys-Glu, (SEQ ID NO: 1)

Glu-Gly-Lys-Gly-Lys-Ser-Val-Val, (SEQ ID NO: 2)

Asp-Gly-Lys-Gly-Lys-Thr, (SEQ ID NO: 3)

Arg-Gly-Lys-Ser, (SEQ ID NO: 4)

Arg-Gly-Lys-Ser-NH$_2$, (SEQ ID NO: 5)

Arg-Gly-Lys-Thr, (SEQ ID NO: 6)

Arg-Gly-Lys-Thr-NH$_2$, (SEQ ID NO: 7)

Lys-Gly-Lys-Ser, (SEQ ID NO: 8)

Lys-Gly-Lys-Ser-NH$_2$, and (SEQ ID NO: 9)

Gly-Lys-Ser-NH$_2$. (SEQ ID NO: 10)

2. The peptide according to claim 1 wherein the peptide corresponds to the SEQ ID NO: 4 sequence.

3. The peptide according to claim 1 wherein the peptide corresponds to the SEQ ID NO: 5 sequence.

4. The peptide according to claim 1, wherein the peptide is solubilized in one or more physiologically acceptable solvents selected from the group consisting of water, glycerol, ethanol, propylene glycol, butylene glycol, dipropylene glycol, ethoxylated diethylene glycol or propoxylated diethylene glycol, cyclic polyols, white petroleum jelly, vegetable oil and combinations thereof.

5. A cosmetic composition comprising at least one peptide derived from human HMG-CoA reductase, wherein the peptide is one of the following sequences:

Glu-Gly-Lys-Gly-Lys-Ser-Val-Val-Cys-Glu, (SEQ ID NO: 1)

Glu-Gly-Lys-Gly-Lys-Ser-Val-Val, (SEQ ID NO: 2)

Asp-Gly-Lys-Gly-Lys-Thr, (SEQ ID NO: 3)

Arg-Gly-Lys-Ser, (SEQ ID NO: 4)

Arg-Gly-Lys-Ser-NH$_2$, (SEQ ID NO: 5)

Arg-Gly-Lys-Thr, (SEQ ID NO: 6)

Arg-Gly-Lys-Thr-NH$_2$, (SEQ ID NO: 7)

Lys-Gly-Lys-Ser, (SEQ ID NO: 8)

Lys-Gly-Lys-Ser-NH$_2$, (SEQ ID NO: 9)

Gly-Lys-Ser-NH$_2$; and (SEQ ID NO: 10)

a physiologically acceptable medium;

wherein the peptide is present in the medium, as an active agent, alone or in combination with at least one other active principle agent.

6. The cosmetic composition according to claim 5, wherein said peptide is present at a concentration of between 0.0005 and 500 ppm.

7. The cosmetic composition according to claim 6, wherein said peptide is present at a concentration of between 0.01 and 5 ppm.

8. The cosmetic composition according to claim 5 wherein the composition is a topically administrable composition in the form of a cream, an oil in water emulsion, a water in oil emulsion, a solution, a suspension, a gel, a milk, a lotion, a stick, or a powder.

9. The cosmetic composition according to claim 5, comprising an effective quantity of the peptide as an active agent that activates human HMG-CoA reductase.

10. A method for cosmetic treatment of skin, the method comprising:

topically applying, to skin to be treated, a composition comprising an effective quantity of a peptide derived from human HMG-CoA reductase, wherein the peptide is one of the following sequences:

(SEQ ID NO: 1)
Glu-Gly-Lys-Gly-Lys-Ser-Val-Val-Cys-Glu, (SEQ ID NO: 2)
Glu-Gly-Lys-Gly-Lys-Ser-Val-Val, (SEQ ID NO: 3)
Asp-Gly-Lys-Gly-Lys-Thr, (SEQ ID NO: 4)
Arg-Gly-Lys-Ser, (SEQ ID NO: 5)
Arg-Gly-Lys-Ser-NH$_2$, (SEQ ID NO: 6)
Arg-Gly-Lys-Thr, (SEQ ID NO: 7)
Arg-Gly-Lys-Thr-NH$_2$, (SEQ ID NO: 8)
Lys-Gly-Lys-Ser, (SEQ ID NO: 9)
Lys-Gly-Lys-Ser-NH$_2$, and (SEQ ID NO: 10)
Gly-Lys-Ser-NH$_2$.

11. The method according to claim 10, wherein the peptide is solubilized in one or more physiologically acceptable solvents selected from the group consisting of water, glycerol, ethanol, propanediol, propylene glycol, butylene glycol, dipropylene glycol, ethoxylated diethylene glycol or propoxylated diethylene glycol, cyclic polyols, white petroleum jelly, vegetable oil, and combinations thereof.

12. The method according to claim 10, wherein the peptide is present at a concentration of between 0.0005 and 500 ppm.

13. The method according to claim 10, wherein the peptide is present at a concentration of between 0.01 and 5 ppm.

14. The method of claim 10, comprising strengthening the barrier function of the epidermis and stimulating epidermal differentiation by topically administering the composition.

15. The method of claim 10, wherein the cosmetic treatment comprises treating against external stresses or cutaneous signs of aging and photo aging.

16. The method of claim 10, wherein the cosmetic treatment comprises treating hypersensitive, irritated or reactive skin.

17. The method of claim 10, wherein the cosmetic treatment comprises treating atopic eczema.

* * * * *